US00PP18945P2

(12) United States Plant Patent
Robacker et al.

(10) Patent No.: US PP18,945 P2
(45) Date of Patent: Jun. 17, 2008

(54) ***ABELIA* PLANT NAMED 'LAVENDER MIST'**

(50) Latin Name: ***Abelia* hybrid**
Varietal Denomination: Lavender Mist

(75) Inventors: Carol Robacker, Peachtree, GA (US); Sloane M. Scheiber, Ocoee, FL (US)

(73) Assignee: University of Georgia Research Foundation, Inc., Athens, GA (US)

( * ) Notice: Subject to any disclaimer, the term of this patent is extended or adjusted under 35 U.S.C. 154(b) by 8 days.

(21) Appl. No.: 11/595,433

(22) Filed: Nov. 9, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Wendy C. Haas
(74) *Attorney, Agent, or Firm*—Greenlee Winner and Sullivan PC

(57) ABSTRACT

A new and distinct *Abelia* hybrid which is characterized by compact upright habit, large compound panicles of fragrant, lavender flowers with straw-green/rose sepals, and green summer foliage turning burgundy purple in the winter.

3 Drawing Sheets

Figure 1:
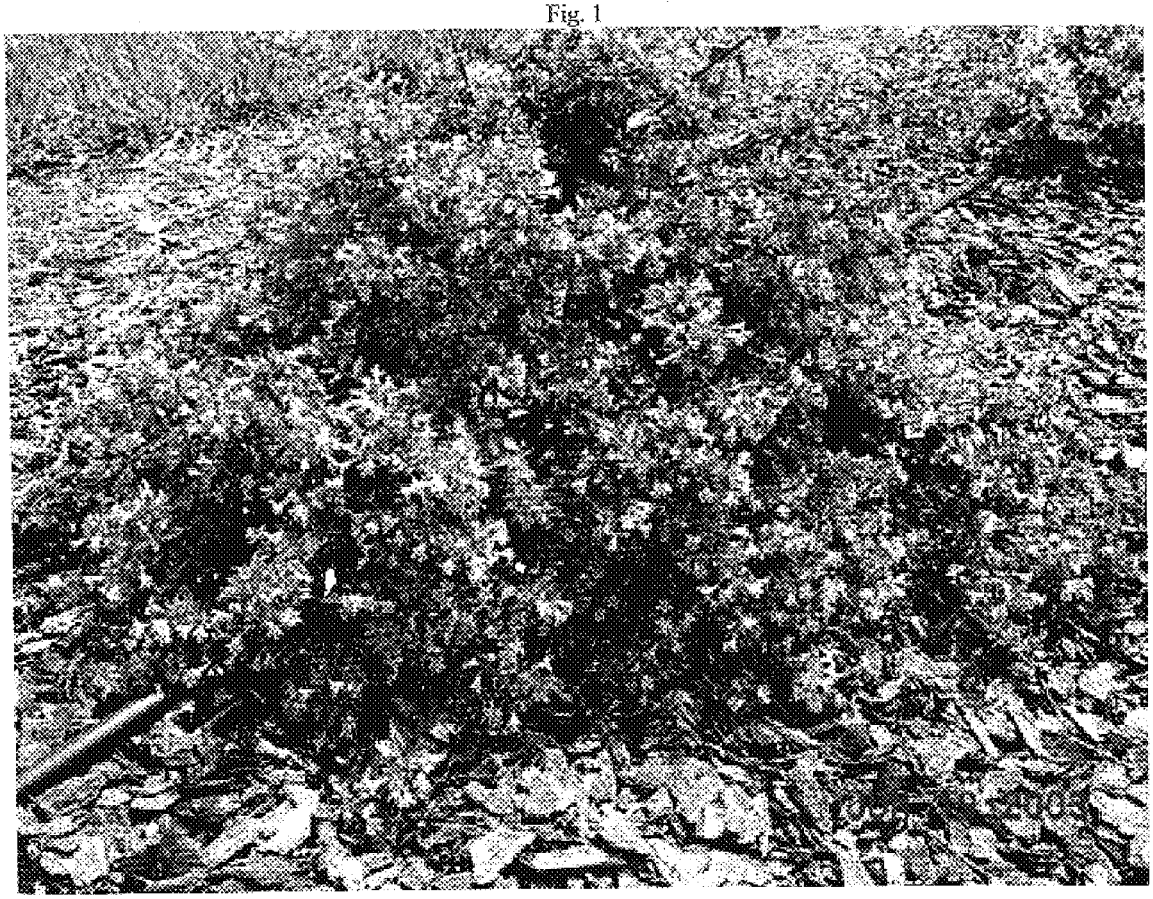

Botanical classification: *Abelia* hybrid.
Varietal denomination: 'Lavender Mist'.

BACKGROUND OF THE INVENTION

The present invention relates to a new and distinct cultivar of the ornamental flowering shrub *Abelia,* hereinafter referred to by the varietal denomination 'Lavender Mist'. 'Lavender Mist' originated from an interspecific cross made in 1998 between the cultivar 'Edward Goucher' (unpatented) and *Abelia chinensis* R. Br. 'Edward Goucher' is a purple-flowered cultivar that was derived from an interspecific cross between *Abelia×grandiflora* and *A. parvifolia* (*schumanii*) and released in 1911. Seeds from the cross were sown in 1999, and eleven seedlings were obtained. These seedlings were planted in a field plot in Griffin, Ga. in the fall of 1999 and were evaluated for three years for flowering and foliage characteristics, plant form and height, cold hardiness and drought tolerance. Plant 99-6-11 was selected among these plants, and assigned the name 'Lavender Mist'.

'Lavender Mist' forms a dense compact shrub with a slight spreading habit. A 4-year old, unpruned, field grown plant measured 159 cm tall and 290 cm wide. Check cultivars 'Compacta' (unpatented), 'Golden Glow' (unpatented), 'Francis Mason' (unpatented), 'Little Richard' (unpatented), and 'Rose Creek' (unpatented) were similar in height, but all less in width.

The foliage color in summer is an attractive dark green. In the fall the leaves on the shoot tips turn burgundy purple, and by mid winter the foliage is dark purple. 'Lavender Mist' is semi-deciduous in USDA Zone 7.

'Lavender Mist' is a heavy bloomer, with clusters of lavender flowers beginning in mid-June and continuing into autumn. Two heavy-blooming periods generally occur in June and again in August, with scattered blooms throughout the rest of the season. The fragrant lavender flowers are borne in compound panicles, averaging 16 cm, long by 14 cm wide. The sepals are straw green at base becoming rose at the tips.

Laboratory evaluations of cold hardiness in Griffin, Ga. during the winter of 2003-04 revealed a mid-winter hardiness of −15 to −17° C., similar to the check cultivars 'Canyon Creek' and 'Rose Creek'. Plants grown in Blairsville and Griffin, Ga. during the 2003-04 winter had no damage.

'Lavender Mist' has drought tolerance typical of *abelia,* and once established grows and blooms without irrigation, although leaf drop occurs under drought stress conditions.

SUMMARY OF THE INVENTION

Plants of cultivar 'Lavender Mist' have not been observed under all possible environmental conditions. The phenotype may vary somewhat with variations in environment such as light-intensity, temperature and cultural conditions, however without any variance in genotype.

The following characteristics have been consistently observed and, to the best knowledge of the inventor, their combination forms the unique characteristics of 'Lavender Mist' as a new and distinct cultivar.

1. Fragrant lavender flowers.
2. Heavy bloomer with large compound panicles on both terminal and axillary shoots.
3. Five sepals per floret, straw-green at base becoming rose at the tip.

'Lavender Mist' is most similar to its parent 'Edward Goucher', but its large compound panicles differ from the small axillary clusters of 'Edward Goucher', and its lavender flowers and dark green leaves differ from the violet flowers and bright green leaves of the parent.

'Lavender Mist' is readily propagated through cuttings. Six-inch cuttings, collected in August, root well in peat-perlite mix under mist. Asexual propagation at Griffin, Ga. since 2001 has shown that the unique characteristics of this new cultivar are stable and reproduced true to type in successive generations.

BRIEF DESCRIPTION OF PHOTOGRAPHS

The accompanying colored photographs illustrate the characteristics of the new cultivar, showing the colors as true as it is reasonably possible to obtain in colored reproductions of this type. Colors in the photograph may differ from the color values listed in the detailed botanical description which accurately describes the colors of the new *abelia*.

FIG. 1. 4 year-old plant showing growth habit and heavy blooming, taken Jun. 19, 2003.

Figure 2:
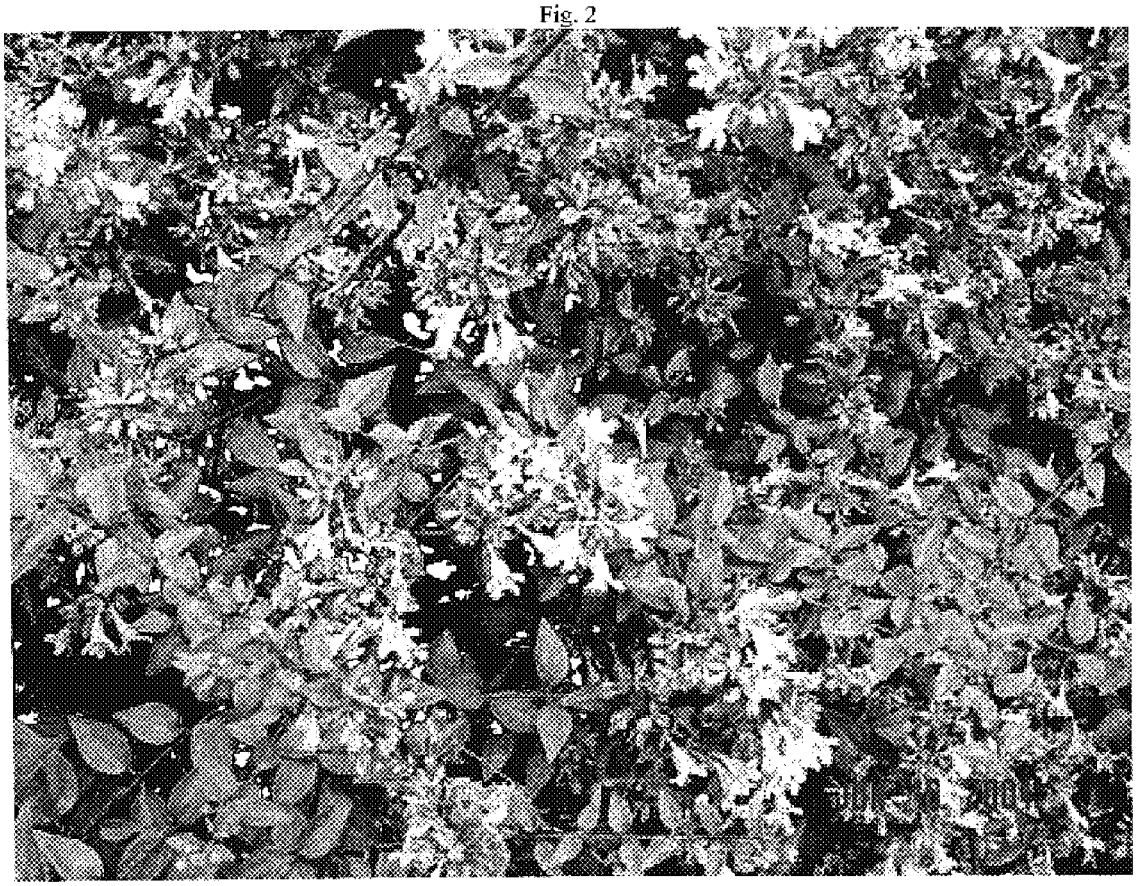

FIG. 2. Lavender flowers against the green leaves giving the foliage a grey-green hue, taken Jun. 16, 2004.

Figure 3:
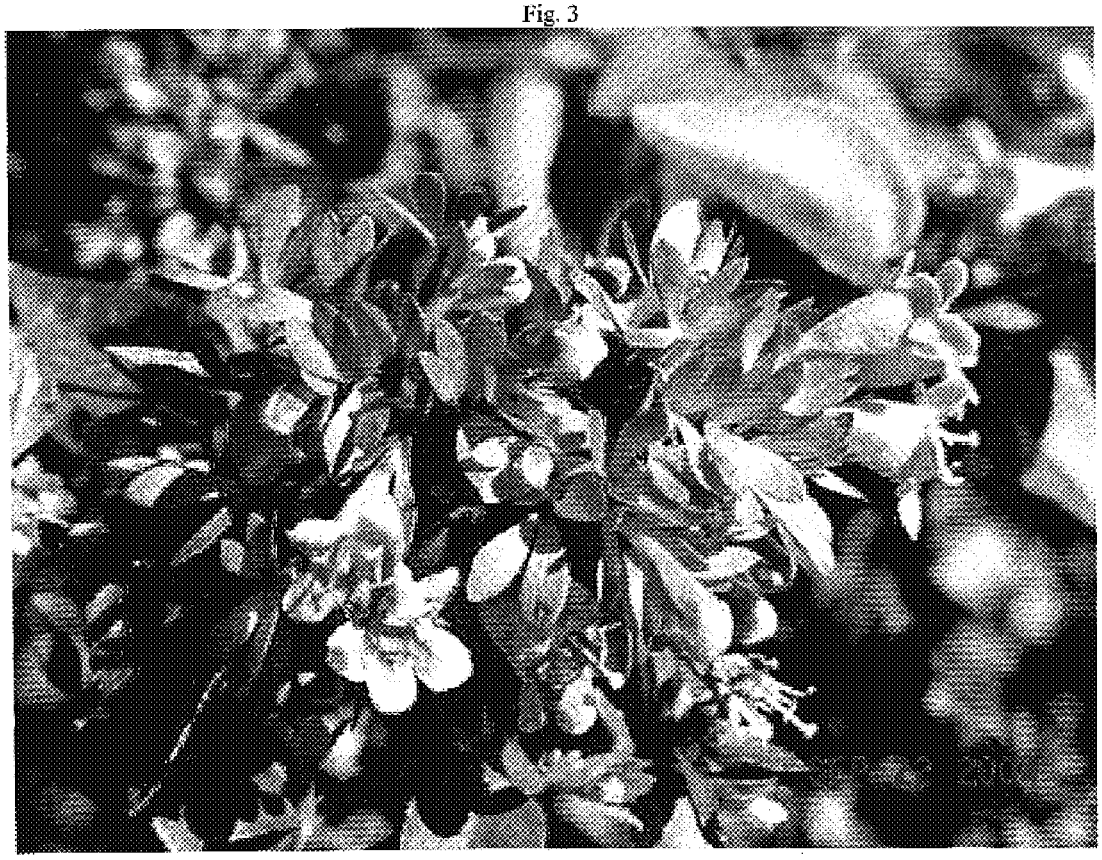

FIG. 3. Lavender flowers with straw-green/rose sepals, taken Sep. 22, 2004.

DETAILED BOTANICAL DESCRIPTION

The botanical description of 'Lavender Mist' is based on 4-year old plants growing in the field in Griffin, Ga. (USDA Zone 7b). Colors are based on The Royal Horticultural Color Chart (2001). Unless otherwise indicated, average measurements, based on 10 to 20 samples, were taken in July/August of 2005.

The plant has a spreading upright habit attaining an average growth height of 159 cm and width of 290 cm after 4-years unpruned growth in the field.

Current year stems are round, 1.5 mm in diameter, puberulent with a mix of short and longer hairs, mostly curved, and are Greyed-Orange 166B in color. The stems show no exfoliation. The average internode length is 17 mm.

Older stems are round, up to 10 to 12 mm in diameter and vary in color from Greyed-Orange 174C to Grey 201B and Brown 200B with maturation. The texture becomes rough with striated exfoliation.

The vegetative buds are opposite, imbricate, lanceolate in shape, 2 mm long by 1 mm wide, with sparse pubescence mainly along the edges, with 3 scales, Greyed-Red 178B in color. There are 2 vegetative buds at each node, at 45° to the stem.

The mature leaf is 26 mm long by 14 mm wide. It is simple, obtusely ovate in shape with an obtuse apex, obtuse base and slightly crenate, almost sinuate margin. The upper surface is mostly glabrous and the lower surface is densely pubescent along the mid vein and sparsely pubescent on the edges and smaller veins. The leaves are slightly waxy, 0.3 mm thick and mostly opposite on the stem. The venation is simple alternate. The main veins are Yellow-Green 145D to Green 139D and the small veins are Greyed-Purple N186A to Yellow-Green 147A in color.

The emerging leaves (March) are Greyed-Orange 166A at the tip and Yellow-Green 144A at the base on the upper surface, and Greyed-Red 178A at the tip on the lower surface. In summer the leaves are Yellow-Green 146A to 147A, or Green 137A on the upper and Green 143C on the lower surface. In the fall the upper surface is Yellow-Green 147A with lower surfaces Green 139D. In winter the upper surface is Greyed-Purple N186A, with lower surface Yellow-Green 145D to Green 139D.

The petiole is slightly curved, slightly convex, 2 to 5 mm in length and 1 to 1.5 mm in diameter, mostly glabrous and Yellow-Green 144A with Yellow-Green 147A edges to Yellow-Green 144B with Greyed-Purple N186A edges.

The flower buds are elongated teardrop in shape, 11 mm long by 4 mm wide, covered in short hairs, some glandular, and Red-Purple 63C in color. The buds show from mid spring to frost.

The inflorescence is a compound panicle, 11 to 20 cm long and 8 to 20 cm wide, with 5 to 10 sub panicles 5 to 8 cm long and 4 to 6 cm wide with a terminal cluster 6 to 10 cm long and 5 to 6 cm wide. The color is Purple 77C at emergence, Purple 77D at full bloom, fading to Purple 76D.

The peduncle has short curved hairs, some glandular, and is Greyed-Orange 176B over Yellow-Green 144B.

There are 200 to 400 flowers at various stages of bloom per inflorescence. The flower is funnel shaped, slightly tubular, and gamopetalous. The whole flower is 18 mm by 14 mm with five lobes rounded and slightly curled. The margin is slightly curled. The base is funnel shaped with a short tube approximately one third the length of the flower. The flower is covered in short hairs, with longer hairs towards the throat of the calyx. At peak of bloom, the color of the upper surface is Purple 77D and the lower surface is Purple 75B.

The pedicels are 4 mm long, with bracteoles and tiny hairs, and Greyed-Orange 176B over Yellow-Green 144B in color.

There are usually 4 sepals, occasionally 5, many gamosepalous with 2 or 3 lobes. They are 6 mm long by 2 mm wide, elliptic in shape with subacute apex, subattenuate base and some with entire margin or with 2 or 3 cells. They are covered in short hairs, and are Red-Purple 63B at the tips, fading to Green 142C at the base, on both upper and lower surfaces.

There are 4 stamens.

The anther is dorsifixed, revolute, 2 mm long by 0.5 mm wide and Yellow-White 158D in color.

The filament is 12 mm long and 0.3 mm wide and has scattered hairs. The color is White N155B.

The pollen color is White N155B.

The pistil is inferior, monostylus, free in shape, 22 mm long by 2 mm wide.

The stigma is circular, dome shaped, punticulate, with clear short hair-like structures and is Yellow-White 158A in color.

The style is tubular in shape, 16 mm long, glabrous, and Orange-White 159D in color.

The single ovary is oval in shape with no pubescence.

The fruit is an achene, a grooved cylindrical capsule in shape, 6 mm long and 2 mm wide with 1 carpel. The color matures from Green 143C to Greyed-Orange 166A.

The seed are cylindrical, grooved longitudinally in shape, 6 mm long by 2 mm wide, covered in short hairs, and are Greyed-Orange 166A in color.

No insect or disease problems have been noted in container plants maintained outside the greenhouse, or in field grown plants.

We claim:

1. A new and distinct cultivar of *abelia* plant named 'Lavender Mist', substantially as illustrated and described.

* * * * *